United States Patent
Rose et al.

Patent Number: 5,104,412
Date of Patent: Apr. 14, 1992

[54] HAIR DYEING COMPOSITIONS

[75] Inventors: David Rose, Hilden; Horst Hoeffkes; Edgar Lieske, both of Duesseldorf, all of Fed. Rep. of Germany

[73] Assignee: Henkel Kommanditgesellschaft auf Aktien, Duesseldorf, Fed. Rep. of Germany

[21] Appl. No.: 635,160

[22] PCT Filed: Jun. 23, 1989

[86] PCT No.: PCT/EP89/00707
§ 371 Date: Feb. 20, 1991
§ 102(e) Date: Feb. 20, 1991

[87] PCT Pub. No.: WO90/00046
PCT Pub. Date: Jan. 11, 1990

[30] Foreign Application Priority Data

Jul. 1, 1988 [DE] Fed. Rep. of Germany ...... 3822365

[51] Int. Cl.$^5$ .............................................. A61K 7/13
[52] U.S. Cl. ................................. 8/405; 8/406; 8/407; 8/408; 8/409; 8/410; 8/412; 8/414; 8/416; 8/425; 8/435
[58] Field of Search .................. 8/405, 406, 407, 408, 8/409, 410, 412, 414, 416, 425, 435

[56] References Cited

FOREIGN PATENT DOCUMENTS 0181505 5/1986 European Pat. Off. .
0211238 2/1987 European Pat. Off. .
2447017 4/1976 Fed. Rep. of Germany .

*Primary Examiner*—A. Lionel Clingman
*Assistant Examiner*—William S. Parks
*Attorney, Agent, or Firm*—Ernest G. Szoke; Wayne C. Jaeschke; Norvell E. Wisdom, Jr.

[57] ABSTRACT

Hair dyeing compositions contain N-cycloalkyl-3-aminophenols corresponding to the following formula

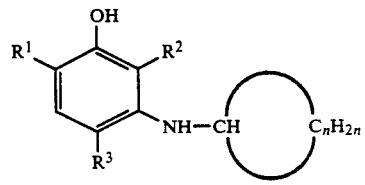

in which n is an integer of 4 to 8 and $R^1$, $R^2$, and $R^3$ independently of one another represent hydrogen, methyl groups or chlorine, or salts thereof as oxidation dye intermediates of the coupler type in addition to typical primary intermediates in a carrier. In conjunction with typical primary intermediates, for example of the p-phenylenediamine derivative type, the new coupler compounds produce shades of brown of high fastness.

16 Claims, No Drawings

HAIR DYEING COMPOSITIONS

BACKGROUND OF THE INVENTION

1. Field of the Invention

This invention relates to hair dyeing compositions based on oxidation dyes. Hair dyeing compositions of the type in question contain oxidation dye intermediates in a cosmetic carrier. The oxidation dye intermediates used are primary intermediates and coupler substances which form dyes under the effect of oxidizing agents or atmospheric oxygen. The cosmetic carriers used for the oxidation dye intermediates are creams, emulsions, gels, shampoos, foam aerosols or other compositions suitable for application to the hair.

2. Statement of Related Art p By virtue of their intense colors and good fastness properties, so-called oxidation dyes, which are formed by the oxidative coupling of one or more primary intermediate components with one another or with one or more coupler components, play a prominent part in the dyeing of hair. The primary intermediates used are normally primary aromatic amines containing another free or substituted hydroxy or amino group in the para position or ortho position, diamino-pyridine derivatives, heterocyclic hydrazone derivatives, 4-aminopyrazolone derivatives, and tetraaminopyrimidines, while the so-called coupler substances are m-phenylene-diamine derivatives, naphthols, resorcinol derivatives and pyrazolones.

Good oxidation dye intermediates have to satisfy above all the following requirements: they must form the required shades with sufficient intensity during the oxidative coupling reaction. In addition, they must be readily absorbed by human hair without excessively staining the scalp. Dye absorption should also be uniform, i.e. the more heavily stressed ends should not be dyed to a greater extent than the less damaged hair roots. The hair colors produced with them should be highly stable to heat, light, and the chemicals used in the permanent waving of hair. Finally, the oxidation hair dye intermediates should be safe to use from the toxicological and dermatological viewpoint.

3-Aminophenols are already known as oxidation dye intermediates, for example from DE-AS 11 43 605, DE-AS 11 51 900, DE 24 47 017 C2 and DE 30 16 882 A1. However, the hair dyeing compositions produced with these products and known primary intermediate components are unsatisfactory with regard to the fastness properties of the hair colors obtained with them. In particular, it is not possible with the known 3-aminophenols to obtain browns of satisfactory naturalness, brilliance, and depth of color.

DESCRIPTION OF THE INVENTION

It has been found that these requirements are satisfied to a high degree by hair dyeing compositions containing oxidation dye intermediates in a carrier which contain as oxidation dye intermediates N-cycloalkyl-3-aminophenols corresponding to formula (I):

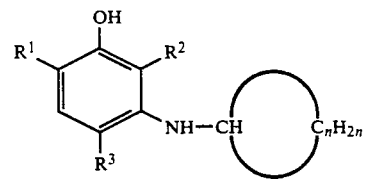

which n is an integer of 4 to 8 and $R^1$, $R^2$ and $R^3$ independently of one another represent hydrogen, methyl groups or chlorine, or salts thereof as coupler components and the primary intermediate components typically used in oxidation hair dyes.

N-Cycloalkyl-3-aminophenols corresponding to formula I in which $R^1$, $R^2$ and $R^3$ represent hydrogen and the group

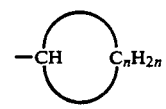

is a cyclopentyl or cyclohexyl group optionally substituted by 1 or 2 methyl groups, are preferred, particularly by virtue of their ready accessibility. The compounds mentioned as examples (coupler components C1, C2 and C3) are particularly preferred.

The N-cycloalkyl-3-aminophenols corresponding to formula I, in which $R^1$, $R^2$ and $R^3$ represent hydrogen, are compounds known from the literature. Their production is known, for example, from EP 181 505 A1. The other N-cycloalkyl-3-aminophenols corresponding to formula I, in which $R^1$, $R^2$ and $R^3$ represent methyl groups or chlorine, may be similarly obtained by the process described therein from the corresponding aminophenol and a cycloalkanone in the presence of a reducing agent in accordance with the following formula scheme:

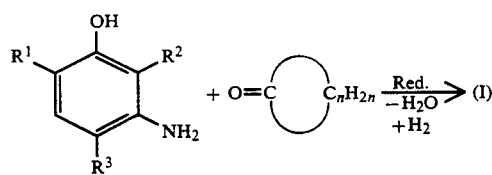

In addition to 3 aminophenol, suitable aminophenols are, for example, 5-chloro-3-aminophenol, 5-chloro-6-methyl-3-aminophenol, 4-chloro-3-aminophenol, 5-methyl-3-aminophenol, 6-methyl-3-aminophenol, 2-methyl-6-aminophenol and 2,6-dimethyl-3-aminophenol. Suitable cycloalkanones are, for example, cyclopentanone, 3-methyl cyclopentanone, cyclohexanone, 3-methyl cyclohexanone, dimethyl cyclopentanone, dimethyl cyclohexanones, isopropyl methyl cyclohexanone, trimethyl cyclopentanones and trimethyl cyclohexanones or cycloheptanone.

The N-cycloalkyl-3-aminophenols corresponding to formula I are valuable coupler compounds which, in conjunction with a number of typical primary intermediate components, form intensive oxidation colors having high stability to light, heat, and cold waving, mainly in shades of brown to blue-violet.

Suitable primary intermediates are any of the known compounds such as, for example, p-phenylenediamine, p-tolylenediamine, N,N-diethyl-2-methyl-p-phenylenediamine, N-ethyl-N-(2-hydroxyethyl)-p- phenylenediamine, chloro-p-phenylenediamine, N,N-bis-(2-hydroxyethyl)-p-phenylenediamine, N,N-dimethyl-p-phenylenediamine, methoxy-p-phenylenediamine, 2,6-dichloro-p-phenylenediamine, 2-chloro-6-bromo-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine, N-2-methoxyethyl-p-phenylenediamine, N-butyl-N-sulfobutyl-p-phenylenediamine and other compounds of the type mentioned which, in addition, may contain one or more $NH_2$ groups, $NHR$ groups, $NR_2$ groups, where R is a $C_{1-4}$ alkyl radical or a $C_{2-4}$ hydroxyalkyl radical; also p-aminophenols, diamino-pyridine derivatives and, in particular, tetraaminopyrimidines, such as 2,4,5,6-tetraaminopyrimidine, 4,5-diamino-2,6-bis-methylaminopyrimidine, 2,5-diamino-4-diethylamino-6-methylaminopyrimidine,2,4,5-triamino-6-piperidinopyrimidine, 2,4,5-triamino-6-anilinopyrimidine, 2,4,5-triamino-6-morpholinopyrimidine, 2,4,5-triamino-6-(2-hydroxyethyl)-aminopyrimidine.

Preferred primary intermediate components are p-phenylenediamine, p-tolylenediamine or derivatives of these compounds or salts thereof.

The N-cycloalkyl-3-aminophenols of formula I to be used in accordance with the invention and the p-phenylenediamine or p-tolylenediamine derivatives suitable as primary intermediate components are be used either as such or in the form of their salts with inorganic or organic acids, for example as chloride, sulfate, phosphate, acetate, propionate, lactate, or citrate.

In addition to the N-cycloalkyl-3-aminophenols corresponding to formula (I), the hair-dyeing compositions according to the invention may also contain other known couplers which are necessary for modifying the shades and for producing natural hues. Known couplers of the type in question include, for example, other m-phenylenediamines, for example 2,4-diaminophenyl-2-hydroxyethyl ether, or phenols, resorcinols, m-aminophenols, naphthols, or pyrazolones. Substantive dyes may also be additionally used for further modifying the shades. Suitable substantive dyes are, for example, nitrophenylenediamines, nitroaminophenols, anthraquinone dyes, or indophenols.

To prepare the hair-dyeing compositions according to the invention, the N-cycloalkyl-3-aminophenols corresponding to formula (I) and the known couplers additionally present, if any, are generally used in substantially molar quantities, based on the primary intermediate components used. Although it has proved best to use molar quantities, a certain excess of individual oxidation dye intermediates is not a disadvantage, so that primary intermediate components and coupler components may be present in a molar ratio of from 1 : 0.5 to 1 : 2.

The N-cycloalkyl-3-aminophenols corresponding to formula (I) and the oxidation dye intermediates or substantive dyes otherwise present in the hair dyeing compositions do not have to be individual chemical compounds. On the contrary, they may also be mixtures of the coupler or primary intermediate components to be used in accordance with the invention.

Basically, the hair color may be oxidatively developed with atmospheric oxygen. However, it is preferred to use a chemical oxidizing agent, particularly when it is desired not only to color, but also to lighten the hair. Particularly suitable oxidizing agents are hydrogen peroxide or adducts thereof with urea, melamine, or sodium borate and also mixtures of such hydrogen peroxide adducts with potassium peroxydisulfate.

To produce the hair-dyeing compositions according to the invention, the oxidation dye intermediates are incorporated into a suitable cosmetic carrier. Examples of suitable cosmetic carriers are creams, emulsions, gels, or even surfactant-containing foaming solutions, for example, shampoos or other compositions which are suitable for application to the hair. Standard ingredients of cosmetic compositions such as these are, for example, wetting agents and emulsifiers, such as anionic, nonionic or ampholytic surfactants, for example soaps, fatty alcohol sulfates, alkanesulfonates, α-olefin sulfonates, fatty alcohol polyglycol ether sulfates, ethylene oxide adducts with fatty alcohols, fatty acids and alkylphenols, sorbitan fatty acid esters and fatty acid partial glycerides, fatty acid alkanolamides; and thickeners, such as for example methyl or hydroxyethyl cellulose; starch: fatty components such as, for example, fatty alcohols, paraffin oils or fatty acid esters; perfume oils; and haircare additives such as, for example, water-soluble cationic polymers, protein derivatives, pantothenic acid, and cholesterol.

The constituents of the cosmetic carriers are used in the usual quantities in the production of hair dyeing compositions according to the invention. For example, emulsifiers are used in concentrations of 0.5 to 30% by weight and thickeners in concentrations of 0.1 to 25% by weight, based on the hair dyeing compositions as a whole.

A particularly suitable carrier is an oil-in-water emulsion containing 0.1 to 25% by weight of a fatty component and 0.5 to 30% by weight of an emulsifier from the group of anionic, nonionic, or ampholytic surfactants.

The oxidation dye intermediates are incorporated into the carrier in quantities of 0.2 to 5% by weight and preferably in quantities of 1 to 3% by weight, based on the hair-dyeing composition as a whole. The content of N-cycloalkyl-3-aminophenols corresponding to formula (I) in the hair dyeing compositions according to the invention may be from about 0.05 to 10 millimol per 100 g of the hair dyeing composition.

The hair dyeing compositions according to the invention may be used in a mildly acidic, neutral, or alkaline medium, irrespective of the type of cosmetic composition used, for example a cream, gel, or shampoo. The hair-dyeing compositions are preferably used at a pH value in the range from 6 to 10 and at temperatures in the range from 15° C. to 40° C. After a contact time of about 30 minutes, the hair-dyeing composition is removed by rinsing from the hair to be dyed. The hair is then washed with a mild shampoo and dried. Washing with a shampoo is unnecessary when a carrier of high surfactant content, for example a dye shampoo, is used.

The following Examples are intended to illustrate the invention without limiting it in any way.

EXAMPLES

Hair dyeing tests

Hair-dyeing compositions according to the invention were prepared in the form of a cream emulsion having the following composition:

| | |
|---|---|
| $C_{12}$-$C_{18}$ fatty alcohol | 10.0 g |
| $C_{12}$-$C_{14}$ fatty alcohol + 2 EO sulfate, Na salt, 28% | 25.0 g |
| Water | 60.0 g |
| Primary intermediate (component E) | 7.5 mmol |

| -continued | |
|---|---|
| Coupler (component C) | 7.5 mmol |
| Na₂SO₃ (inhibitor) | 1.0 g |
| Concentrated ammonia solution | to pH = 9.5 |
| Water | ad 100 g |

The constituents were mixed together in the above order. After addition of the oxidation dye intermediates and the inhibitor, the pH value of the emulsion was first adjusted to 9.5 with concentrated ammonia solution, after which the emulsion was made up with water to 100 g.

The hair color was oxidatively developed with 3% hydrogen peroxide solution as oxidizing agent. To this end, 50 g of hydrogen peroxide solution (3%) were added to and mixed with 100 g of the emulsion.

The dye cream was applied to approximately 5 cm long strands of standardized, 90% grey, but not specially pretreated human hair and left thereon for 30 minutes at 27° C. After dyeing, the hair was rinsed, washed with a standard shampoo and then dried.

The following N-cycloalkyl-3-aminophenols were used as the couplers (component C):
C1: N-cyclopentyl-3-aminophenol
C2: N-cyclohexyl-3-aminophenol
C3 N-(3-methylcyclohexyl)-3-aminophenol The following compounds were used as the primary intermediate component (component D):
D1: p-phenylenediamine
D2: p-tolylenediamine
D3: N,N-diethyl-p-phenylenediamine
D4: N,N-bis-(δ-hydroxyethyl)-p-phenylenediamine
D5: N-(δ-hydroxyethyl)-p-phenylenediamine
D6: 2-chloro-p-phenylenediamine
D7: 2,5-diaminobenzyl alcohol
D8: 2-(2,5-diaminophenyl)-ethanol
D9: 1,2-bis-(4-aminophenyl)-ethylenediamine
D10: 2,5-diaminophenyl-δ-ethoxyethyl ether
D11: p-aminophenol
D12: 2,4,5,6-tetraaminopyrimidine
D13: 2-dimethylamino-4,5,6-triaminopyrimidine The hair colors obtained with these oxidation dye intermediates in the combinations listed in Table 1 are shown in that Table.

TABLE 1

| Example No. | Primary Intermediate | Coupler Component | Shade Obtained |
|---|---|---|---|
| 1 | D1 | C1 | Aubergine |
| 2 | D2 | C1 | Brown-black |
| 3 | D3 | C1 | Black-blue |
| 4 | D4 | C1 | Black-blue |
| 5 | D5 | C1 | Dark violet |
| 6 | D6 | C1 | Dark brown |
| 7 | D8 | C1 | Grey-brown |
| 8 | D11 | C1 | Brown |
| 9 | D12 | C1 | Blue-violet |
| 10 | D13 | C1 | Blue-grey |
| 11 | D2 | C2 | Brown-black |
| 12 | D12 | C2 | Dark violet |
| 13 | D7 | C3 | Grey-brown |
| 14 | D9 | C3 | Grey-brown |
| 15 | D10 | C3 | Dark-violet |

What is claimed is:

1. Hair dyeing compositions comprising a carrier which is suitable for application to the hair and:
(A) N-cycloalkyl-3-aminophenols or salts thereof, said N-cycloalkyl-3-aminophenols corresponding to the formula

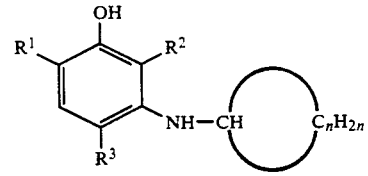

in which n is an integer of 4 to 8 and $R^1$, $R^2$, and $R^3$ independently of one another represent hydrogen, methyl groups or chlorine as coupler components; and
(B) primary intermediate components.

2. Hair dyeing compositions as claimed in claim 1, wherein $R^1$, $R^2$, and $R^3$ represent hydrogen and the moiety is selected from the group consisting of cyclopentyl, cyclohexyl, methyl cyclopentyl, methyl cyclohexyl, dimethyl cyclopentyl, and dimethyl cyclohexyl.

3. Hair dyeing compositions as claimed in claim 2, comprising p-phenylenediamine, p-tolylenediamine, or derivatives of these compounds or salts thereof as primary intermediate components.

4. Hair dyeing compositions as claimed in claim 3, comprising an oil-in-water emulsion containing 0.1 to 25% by weight of a fatty component and 0.5 to 30% by weight of an emulsifier from the group of anionic, nonionic or ampholytic surfactants as carrier and said N-cycloalkyl-3-aminophenols in a quantity of 0.05 to 10 millimol per 100 g of the hair dyeing composition.

5. Hair dyeing compositions as claimed in claim 1, comprising p-phenylenediamine, p-tolylenediamine, or derivatives of these compounds or salts thereof as primary intermediate components.

6. Hair dyeing compositions as claimed in claim 5, comprising an oil-in-water emulsion containing 0.1 to 25% by weight of a fatty component and 0.5 to 30% by weight of an emulsifier from the group of anionic, nonionic or ampholytic surfactants as carrier and said N-cycloalkyl-3-aminophenols in a quantity of 0.05 to 10 millimol per 100 g of the hair dyeing composition.

7. Hair dyeing compositions as claimed in claim 2, comprising an oil-in-water emulsion containing 0.1 to 25% by weight of a fatty component and 0.5 to 30% by weight of an emulsifier from the group of anionic, nonionic or ampholytic surfactants as carrier and said N-cycloalkyl-3-aminophenols in a quantity of 0.05 to 10 millimol per 100 g of the hair dyeing composition.

8. Hair dyeing compositions as claimed in claim 1, comprising an oil-in-water emulsion containing 0.1 to 25% by weight of a fatty component and 0.5 to 30% by weight of an emulsifier from the group of anionic, nonionic or ampholytic surfactants as carrier and said N-cycloalkyl-3-aminophenols in a quantity of 0.05 to 10 millimol per 100 g of the hair dyeing composition.

9. Hair dyeing compositions as claimed in claim 8, wherein said N-cycloalkyl-3-aminophenols are selected from the group consisting of N-cyclopentyl-3-aminophenol, N-cyclohexyl-3-aminophenol, and N-(3-methylcyclohexyl)-3-aminophenol.

10. Hair dyeing compositions as claimed in claim 7, wherein said N-cycloalkyl-3-aminophenols are selected from the group consisting of N-cyclopentyl-3-aminophenol, N-cyclohexyl-3-aminophenol, and N-(3-methylcyclohexyl)-3-aminophenol.

11. Hair dyeing compositions as claimed in claim 6, wherein said N-cycloalkyl-3-aminophenols are selected from the group consisting of N-cyclopentyl-3-aminophenol, N-cyclohexyl-3-aminophenol, and N-(3-methylcyclohexyl)-3-aminophenol.

12. Hair dyeing compositions as claimed in claim 5, wherein said N-cycloalkyl-3-aminophenols are selected from the group consisting of N-cyclopentyl-3-aminophenol, N-cyclohexyl-3-aminophenol, and N-(3-methylcyclohexyl)-3-aminophenol.

13. Hair dyeing compositions as claimed in claim 4, wherein said N-cycloalkyl-3-aminophenols are selected from the group consisting of N-cyclopentyl-3-aminophenol, N-cyclohexyl-3-aminophenol, and N-(3-methylcyclohexyl)-3-aminophenol.

14. Hair dyeing compositions as claimed in claim 3, wherein said N-cycloalkyl-3-aminophenols are selected from the group consisting of N-cyclopentyl-3-aminophenol, N-cyclohexyl-3-aminophenol, and N-(3-methylcyclohexyl)-3-aminophenol.

15. Hair dyeing compositions as claimed in claim 2, wherein said N-cycloalkyl-3-aminophenols are selected from the group consisting of N-cyclopentyl-3-aminophenol, N-cyclohexyl-3-aminophenol, and N-(3-methylcyclohexyl)-3-aminophenol.

16. Hair dyeing compositions as claimed in claim 1, wherein said N-cycloalkyl-3-aminophenols are selected from the group consisting of N-cyclopentyl-3-aminophenol, N-cyclohexyl-3-aminophenol, and N-(3-methylcyclohexyl)-3-aminophenol.

* * * * *

UNITED STATES PATENT AND TRADEMARK OFFICE
CERTIFICATE OF CORRECTION

PATENT NO. : 5,104,412

DATED : April 14, 1992

INVENTOR(S) : Rose et al.

It is certified that error appears in the above-identified patent and that said Letters Patent is hereby corrected as shown below:

In claim 2, column 6, line 17, after the word moiety insert the formula--

--.

Signed and Sealed this

Twenty-fourth Day of August, 1993

Attest:

BRUCE LEHMAN

*Attesting Officer*    *Commissioner of Patents and Trademarks*